US009259546B2

(12) United States Patent
Garde et al.

(10) Patent No.: US 9,259,546 B2
(45) Date of Patent: Feb. 16, 2016

(54) VENTILATOR WITH INTEGRATED BLOWER TO PROVIDE NEGATIVE OR POSITIVE PRESSURE IN A VENTILATOR SYSTEM

(75) Inventors: Smita Garde, Irvine, CA (US); Mabini Arcilla, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 264 days.

(21) Appl. No.: 13/994,940

(22) PCT Filed: Dec. 16, 2011

(86) PCT No.: PCT/IB2011/055734
§ 371 (c)(1),
(2), (4) Date: Jun. 17, 2013

(87) PCT Pub. No.: WO2012/085792
PCT Pub. Date: Jun. 28, 2012

(65) Prior Publication Data
US 2013/0276789 A1    Oct. 24, 2013

Related U.S. Application Data

(60) Provisional application No. 61/425,493, filed on Dec. 21, 2010.

(51) Int. Cl.
| | | |
|---|---|---|
| *A61M 11/00* | (2006.01) | |
| *A61M 16/04* | (2006.01) | |
| *A61M 16/00* | (2006.01) | |
| *A61M 16/06* | (2006.01) | |

(Continued)

(52) U.S. Cl.
CPC ........... *A61M 16/04* (2013.01); *A61M 16/0009* (2014.02); *A61M 16/0051* (2013.01);
(Continued)

(58) Field of Classification Search
CPC .................. A61M 16/0051; A61M 2230/005; A61M 2016/0027; A61M 16/0069; A61M 2016/0036; A61M 2016/0039; A61M 16/0003; A61M 16/06; A61M 16/0057; A61M 16/04; A61M 16/0066; A61M 2202/0208; A61M 2202/025; A61M 16/0816; A61M 16/0875; A61M 16/12; A61M 16/208; A61M 16/009
USPC ........................................ 128/204.18–204.23
See application file for complete search history.

(56) References Cited

U.S. PATENT DOCUMENTS

| 2,484,306 A | 10/1949 | McClain |
| 4,224,940 A | 9/1980 | Monnier |

(Continued)

FOREIGN PATENT DOCUMENTS

| DE | 946258 C1 | 7/1956 |
| EP | 0862922 A1 | 9/1998 |
| FR | 2344278 A1 | 10/1977 |

*Primary Examiner* — Steven Douglas

(57) ABSTRACT

A ventilator system (100/200/300/400) includes an integrated blower (130/230/330). In one case, the ventilator system includes: an inspiration port (122/222/322) for connection to an inspiratory limb (112/212/312) of a dual-limb patient circuit (110/210/310), and an expiration port (142/242/342) for connection to an expiratory limb (114/214/314) of the dual-limb patient circuit; a gas delivery device (120/220/320) connected to the inspiration port to supply a pressurized flow of gas to the inspiration port to generate a positive pressure; and a blower having an inlet (132/232/332) that is operatively connected to the expiration port and configured to be controlled to selectively supply a negative pressure level between 4 and 120 cmH$_2$O to the expiration port, and an outlet (134/234/334) to exhaust gas received from the expiration port. In another case, the ventilator system includes a blower to generate positive pressure/flow to augment flow for noninvasive ventilation.

7 Claims, 4 Drawing Sheets

(51) Int. Cl.
*A61M 16/08* (2006.01)
*A61M 16/12* (2006.01)
*A61M 16/20* (2006.01)

(52) U.S. Cl.
CPC ....... *A61M16/0066* (2013.01); *A61M 16/0069* (2014.02); *A61M 16/06* (2013.01); *A61M 16/0816* (2013.01); *A61M 16/0875* (2013.01); *A61M 16/12* (2013.01); *A61M 16/208* (2013.01); *A61M 2016/0027* (2013.01); *A61M 2016/0039* (2013.01); *A61M 2202/025* (2013.01); *A61M 2202/0208* (2013.01)

(56) References Cited

U.S. PATENT DOCUMENTS

| | | | | |
|---|---|---|---|---|
| 6,076,523 | A * | 6/2000 | Jones et al. | 128/205.11 |
| 6,860,265 | B1 | 3/2005 | Emerson | |
| 7,497,215 | B1 * | 3/2009 | Nguyen et al. | 128/204.17 |
| 2002/0053345 | A1 * | 5/2002 | Jafari et al. | 128/204.23 |
| 2003/0015200 | A1 | 1/2003 | Hansen | |
| 2007/0144516 | A1 * | 6/2007 | Doyle | 128/204.18 |
| 2008/0168989 | A1 * | 7/2008 | Cewers | 128/204.21 |

* cited by examiner

VENTILATOR WITH INTEGRATED BLOWER TO PROVIDE NEGATIVE OR POSITIVE PRESSURE IN A VENTILATOR SYSTEM

TECHNICAL FIELD

This invention pertains to ventilators, and in particular, to a ventilator including an integrated blower to provide negative or positive pressure in a ventilator system.

BACKGROUND AND SUMMARY

Ventilators are used in a variety of settings. For example, in a hospital a patient may be ventilated as part of their medical care. In particular, ventilators are commonly provided in hospital intensive care units (ICUs).

Many of these ventilators use high pressure or compressed gas source for breath delivery. In addition to generating and delivering breaths to the patient, a high-end ventilator may include an integrated system implementation. With such an implementation, a ventilator system can include other patient care modalities like secretion management and high frequency ventilation etc. These modalities require both positive pressure and negative pressure in the system for effective implementation. For example, in high frequency positive pressure ventilation (HFPPV), positive pressure is generated from the high pressure, compressed, gas source and negative pressure is generated by a venturi system implementation.

For example, for an HFPPV implementation, the mean airway pressure (MAP) depends on the peak-to-peak amplitude of the positive pressure pulses. For higher frequencies or for higher amplitudes, the MAP may be too high for the patient. MAP can only be lowered by applying negative pressure during exhalation. This negative pressure may be generated by a venturi effect from the positive pressure side of the system. However, a venturi system is very noisy and it has a relatively slow response. In another modality such as secretion management, a ventilator system needs to deliver insufflation (positive pressure) and exsufflation (negative pressure) to simulate a cough. In yet another modality such as noninvasive ventilation incorporated in high-end ICU ventilators, a blower can additionally augment and/or provide higher flows of gas that may be needed for such ventilation therapy. The gas supplied from individual gas outlets in the hospitals may be limited to ~180 liters per minute (lpm) and is adequate for the most invasive mechanical ventilation needs. However, for non-invasive ventilation, the ventilator should be able to generate much higher flows—on the order of 250 to 300 liters/minute (lpm) to compensate for mask leaks.

Accordingly, it would be desirable to provide a ventilator and method of ventilation which can address one or more of these requirements.

In one aspect of the invention, a ventilator system comprises: an inspiration port configured to be connected to an inspiratory limb of a dual-limb patient circuit, and an expiration port configured to be connected to an expiratory limb of the dual-limb patient circuit; a gas delivery device operatively connected to the inspiration port and configured to supply a pressurized flow of gas to the inspiration port to generate positive pressure; and a blower having an inlet that is operatively connected to the expiration port and configured to be controlled to selectively supply a negative pressure level between 4 and 120 $cmH_2O$ to the expiratory limb, and further having an outlet configured to exhaust gas received via the expiration port.

In another aspect of the invention, a method of ventilation comprises: providing an inspiration port configured to be connected to an inspiration limb of a dual-limb patient circuit, and providing an expiration port configured to be connected to an expiratory limb of the dual-limb patient circuit; supplying a pressurized flow of gas to the inspiration port to generate positive pressure; and selectively connecting an inlet of a blower to the expiration port to selectively supply a negative pressure level between 4 and 120 $cmH_2O$ to the expiration port and to exhaust from an outlet of the blower gas received from the expiration port.

In yet another aspect of the invention, a ventilator system comprises: a patient circuit interface port configured to be connected to a single-limb patient circuit; a gas delivery device operatively connected to the patient circuit interface port and configured to supply a pressurized flow of gas to the patient circuit interface port to generate positive pressure; a blower having an outlet operatively connected to the patient circuit interface port and configured to supply a pressurized flow of air to the patient circuit interface port to generate positive pressure; a pressure transducer configured to measure a patient airway pressure; at least one flow sensor configured to measure a gas flow in the patient circuit; and a controller configured to control the gas delivery device and the blower in response to a pressure transducer signal indicating the measured pressure in the patient circuit and a flow sensor signal indicating the measured gas flow from the gas delivery device.

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

Figure 1:
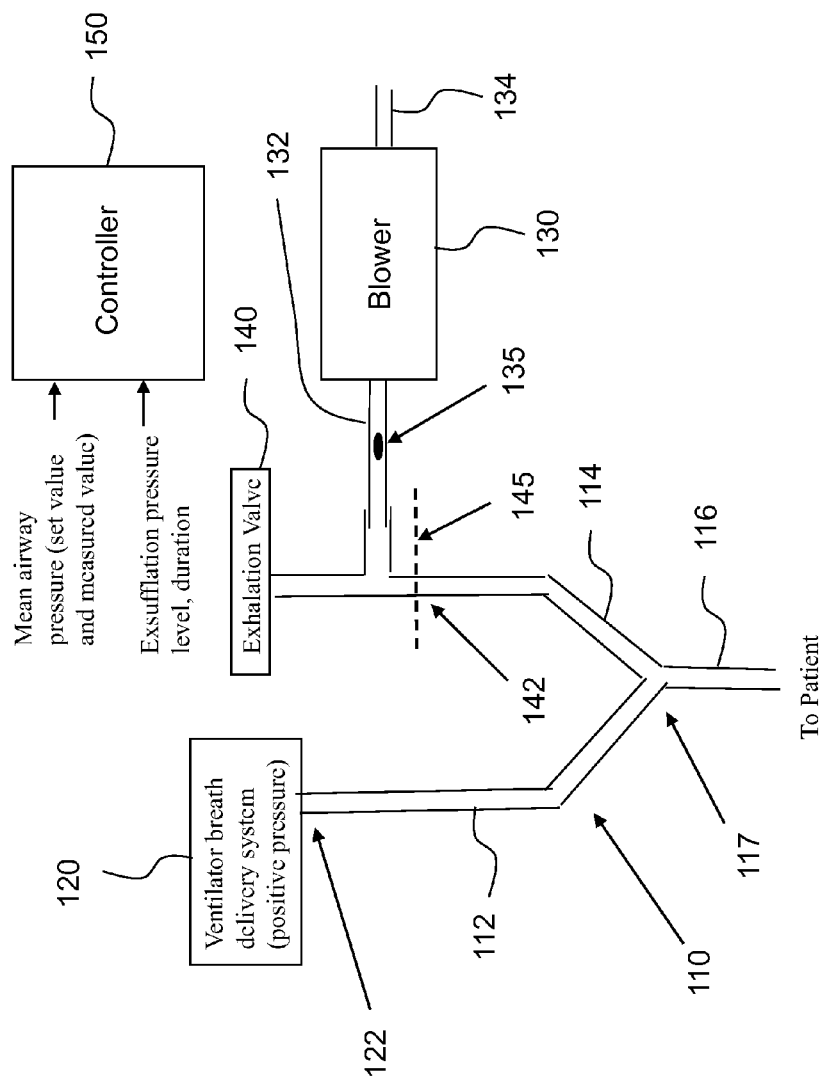
FIG. 1 is a functional block diagram of a ventilator system that includes a blower to generate negative pressure in the system.

FIG. 1 is a functional block diagram of a ventilator system 100. Ventilator system 100 includes a dual-limb patient circuit 110, a gas delivery device 120, a blower 130, an exhalation valve 140 and a controller 150.

Dual-limb patient circuit 110 includes an inspiratory limb 112, an expiratory limb 114, a Y-connector 117, and a breathing tube 116 connected to inspiratory limb 112 and expiratory limb 114 via Y-connector 117. In some embodiments, breathing tube 116 may be an endotracheal tube.

Gas delivery device 120 is a device configured to supply a pressurized flow of gas to inspiratory limb 112 of dual-limb patient circuit 110 via inspiratory port 142 to generate positive pressure. Here, the gas may be a mixture of constituent gases, for example, air, oxygen, heliox, etc. In some embodiments, gas delivery device 120 is configured to receive pressurized gas from an external supply (e.g., a tank or through a wall outlet) and to control and/or regulate the flow of gas to patient circuit 110. Gas delivery device 120 may include one or more valves and regulators.

Blower 130 has an inlet 132 which is configured in operation to receive gas from expiratory limb 114 of dual-limb patient circuit 110 via an expiratory port 142, and further has an outlet 134 for exhausting gas received from expiratory limb 114. Here, a "blower" is defined as any electromechanical device that generates pressurized flow of gas by rotational movement of a surface(s) e.g. rotating blades and which can provide a negative pressure of between 4 and 120 $cmH_2O$ at its inlet 132. As example, a blower may comprise a rotating impeller or high speed fan. A blower leak port 135 is provided at the inlet side of blower 130.

Exhalation valve 140 operates to selectively connect inlet 132 of blower 130 to expiratory port 142, for example during an exhalation phase of a breathing cycle, as will be discussed in greater detail with respect to FIGS. 2A-2C. Exhalation valve 140 is provided with a diaphragm 145.

In response to one or more input signals and/or programmed parameters, controller 150 controls blower 130 and exhalation valve 140 to provide ventilation for a patient 10. For example, controller 130 may control the mean airway pressure in high frequency positive pressure ventilation (HFPPV) to maintain a target mean airway pressure as set by the user. In another example, for providing insufflation-exsufflation for secretion management of the patient, controller 150 may control the patient airway pressure during exsufflation.

The provision of blower 130 in ventilator 100 provides for several possible features and benefits in various operating modes. Some example embodiments will be explained with respect to the detailed illustrations of FIGS. 2A-2C and 3A-3C, and FIG. 4.

Figure 2:
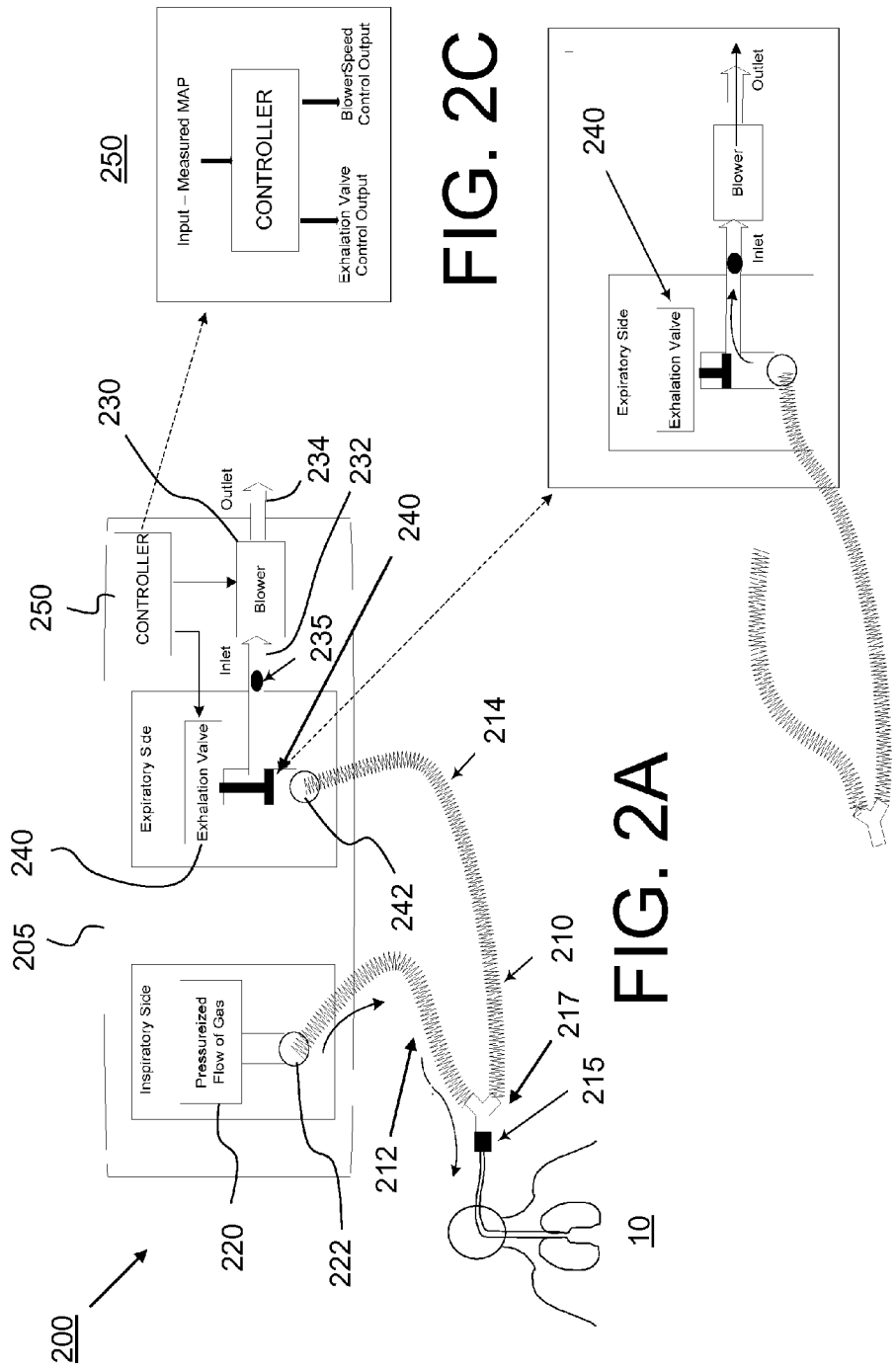
FIG. 2A is a detailed illustration of a first example embodiment of a ventilator system that includes a blower, during a first phase of a breathing cycle.
FIG. 2B is a detailed illustration of the first example embodiment of FIG. 2A, during a second phase of a breathing cycle.
FIG. 2C is a detailed illustration of the controller of FIG. 2A.

FIGS. 2A-2C illustrate a first example embodiment of a ventilator where an integrated blower may be used to generate negative pressure for control of mean airway pressure (MAP) for HFPPV. In this case, in some embodiments the blower continuously generates low to moderate levels of negative pressure for the expiratory limb of a dual-limb patient circuit.

FIG. 2A is a detailed illustration of a first example embodiment 200 of a ventilator system during a first (inhalation) phase of a breathing cycle. Ventilator system 200 comprises a ventilator 205 with an integrated blower 230, and a dual-limb patient circuit 210.

Ventilator 205 includes a gas delivery device 220, blower 230, an exhalation valve 240, and a controller 250.

Dual-limb patient circuit 210 includes an inspiratory limb 212, an expiratory limb 214, a Y-connector 217, and a breathing tube connected to inspiratory limb 212 and expiratory limb 214 via Y-connector 217. In some embodiments, the breathing tube may be an endotracheal tube. A pressure transducer 215 is connected to Y-connector 217 for measuring a patient airway pressure provided to patient 10. Pressure transducer 215 generates a measured patient airway pressure signal which is provided to controller 250. Gas delivery device 220 is a device configured to supply a pressurized flow of gas to inspiratory limb 212 of dual-limb patient circuit 210 via inspiratory port 222 to generate positive pressure. Here, the gas may be a mixture of constituent gases, for example, air, oxygen, heliox, etc. In some embodiments, gas delivery device 220 is configured to receive pressurized gas from an external supply (e.g., a tank or through a wall outlet) and to control and/or regulate the flow of gas to patient circuit 210. Gas delivery device 220 may include one or more flow control valves and/or regulators.

Blower 230 has an inlet 232 which is configured in operation to receive gas from expiratory limb 214 of dual-limb patient circuit 210 via an expiratory port 242, and further has an outlet 234 for exhausting gas received from expiratory limb 214. A blower leak port 235 is provided at the inlet side of blower 230.

As illustrated in FIG. 2A, in the first (inhalation) phase of the breathing cycle, controller 250 controls exhalation valve 240 to close off a pathway from expiration limb 214 via expiratory port 242 to inlet 232 of blower 230. In some embodiments controller 250 may turn off, reduce the speed, or reduce the blower-current for blower 230 during the first (inhalation) phase of the breathing cycle.

FIG. 2B is a detailed illustration of the second example embodiment ventilator system 200 during a second (exhalation) phase of a breathing cycle. As can be seen in FIG. 2B, during the second (exhalation) phase of the breathing cycle, controller 250 controls exhalation valve 240 to open a pathway from expiratory port 242 to inlet 232 of blower 230, and controls blower 230 to operate to receive gas from expiration limb 214 via expiratory port 242 at blower inlet 232 and to exhaust the gas from blower outlet 234. In some embodiments, controller 250 provides a signal to blower 230 to vary or control the operating speed of blower 230 and thereby adjust or control the negative pressure supplied by blower 230.

FIG. 2C is a detailed illustration of controller 250 of FIG. 2A. Controller 250 receives a measured patient airway pressure, for example from pressure transducer 215, and supplies output signals for controlling blower 230 and exhalation valve 240. In some embodiments, controller 250 calculates or determines a mean airway pressure (MAP) from the measured patient airway pressure signal, received for example from transducer 215. In some embodiments, controller 250 provides the output signals for controlling blower 230 and exhalation valve 240 to maintain the calculated MAP at or near a target MAP.

Figure 3:
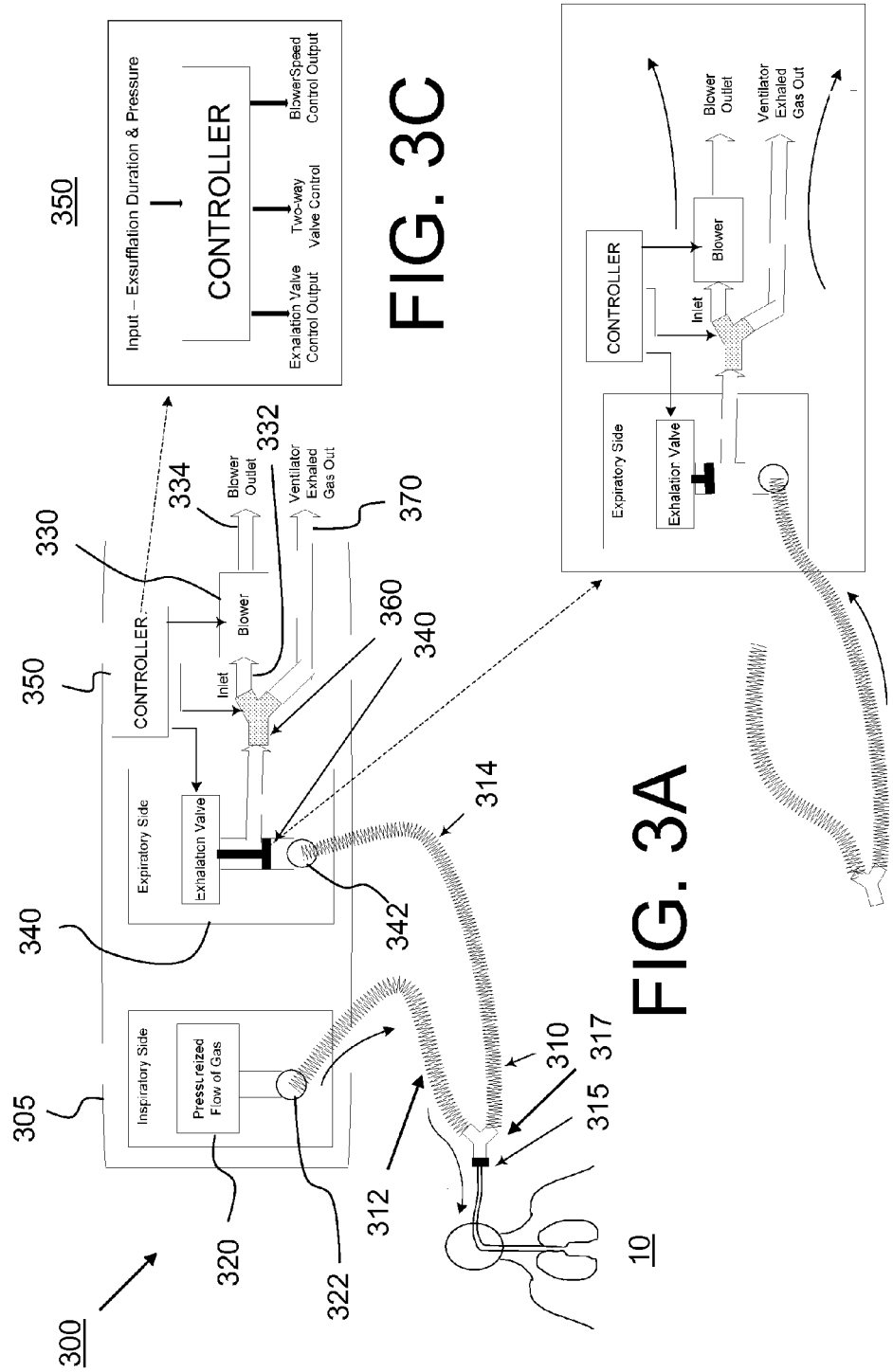
FIG. 3A is a detailed illustration of a second example embodiment of a ventilator system that includes a blower, during a first phase of a breathing cycle.
FIG. 3B is a detailed illustration of the example of the second example embodiment of FIG. 3A, during a second phase of a breathing cycle.
FIG. 3C is a detailed illustration of the controller of FIG. 3A.

FIGS. 3A-3C illustrate a second example embodiment of a ventilator system where an integrated blower may be used to generate negative pressure for exsufflation for secretion management for invasive ventilation. In some embodiments, the blower generates high levels of negative pressure for very brief durations at an inhalation-to-exhalation transition when the ventilator operates in a secretion management mode.

FIG. 3A is a detailed illustration of a second example embodiment 300 of a ventilator system during a first (inhalation) phase of a breathing cycle. Ventilator system 300 comprises a ventilator 305 with an integrated blower 330, and a dual-limb patient circuit 310.

Ventilator 305 includes a gas delivery device 320, blower 330, an exhalation valve 340, a controller 350, a two-way valve 360, and a ventilator exhaust port 370. In some embodiments, the implementation of the two-way valve 360 may be integrated with the exhalation valve 340.

Dual-limb patient circuit 310 includes an inspiratory limb 312, an expiratory limb 314, a Y-connector 317, and a breathing tube connected to inspiratory limb 312 and expiratory limb 314 via Y-connector 317. In some embodiments, the breathing tube may be an endotracheal tube. A pressure transducer 315 is used for measuring a patient airway pressure provided to patient 10. Pressure transducer 315 generates a measured patient airway pressure signal which is provided to controller 350.

Gas delivery device 320 is a device configured to supply a pressurized flow of gas to inspiratory limb 312 of dual-limb patient circuit 310 via inspiratory port 322 to generate positive pressure. Here, the gas may be a mixture of constituent gases, for example, air, oxygen, heliox, etc. In some embodiments, gas delivery device 320 is configured to receive pressurized gas from an external supply (e.g., a tank or through a wall outlet) and to control and/or regulate the flow of gas to patient circuit 310. Gas delivery device 320 may include one or more flow valves and/or regulators.

Blower 330 has an inlet 332 which is configured in operation to receive gas from expiratory limb 314 of dual-limb patient circuit 310 via an expiratory port 342, and further has an outlet 334 for exhausting gas received from expiratory limb 314.

As illustrated in FIG. 3A, in the first (inhalation) phase of the breathing cycle, controller 350 controls exhalation valve 340 to close off a pathway from expiration limb 314 via expiratory port 342 to two-way valve 360. In some embodiments controller 350 may turn off, reduce the speed, or reduce blower-current for blower 330 during the first (inhalation) phase of the breathing cycle.

FIG. 3B is a detailed illustration of the second example embodiment ventilator system 300 during a second (exhalation) phase of the breathing cycle. As can be seen in FIG. 3B, during the second (exhalation) phase of the breathing cycle, controller 350 controls exhalation valve 340 to open a pathway from expiratory port 344 to two-way valve 360. Furthermore, in some embodiments, during an exsufflation period of an exhalation phase of a breathing cycle (e.g., during an-inhalation-to-exhalation transition), controller 350 controls two-way valve 360 to connect inlet 332 of blower 330 to expiration limb 314 via expiratory port 344, and controls blower 330 to exhaust gas from blower outlet 334 to simulate cough to mobilize secretion. Also, during a remainder of the exhalation phase of the breathing cycle, controller 350 controls two-way valve 360 to connect ventilator exhaust port 370 to expiration limb 314 via expiratory port 342. In some embodiments, controller 350 provides a signal to blower 330 to vary or control the operating speed and supply current of blower 330 and thereby adjust or control the negative pressure supplied by blower 330.

FIG. 3C is a detailed illustration of the controller 350 of FIG. 3A. Controller 350 receives a measured patient airway pressure signal, for example from pressure transducer 315, and supplies output signals for controlling blower 330, exhalation valve 340, and two-way valve 360. In some embodiments, controller 350 provides the output signals for controlling blower 330 and exhalation valve 340 to provide the target exsufflation pressure and pressure during exhalation phase.

Figure 4:
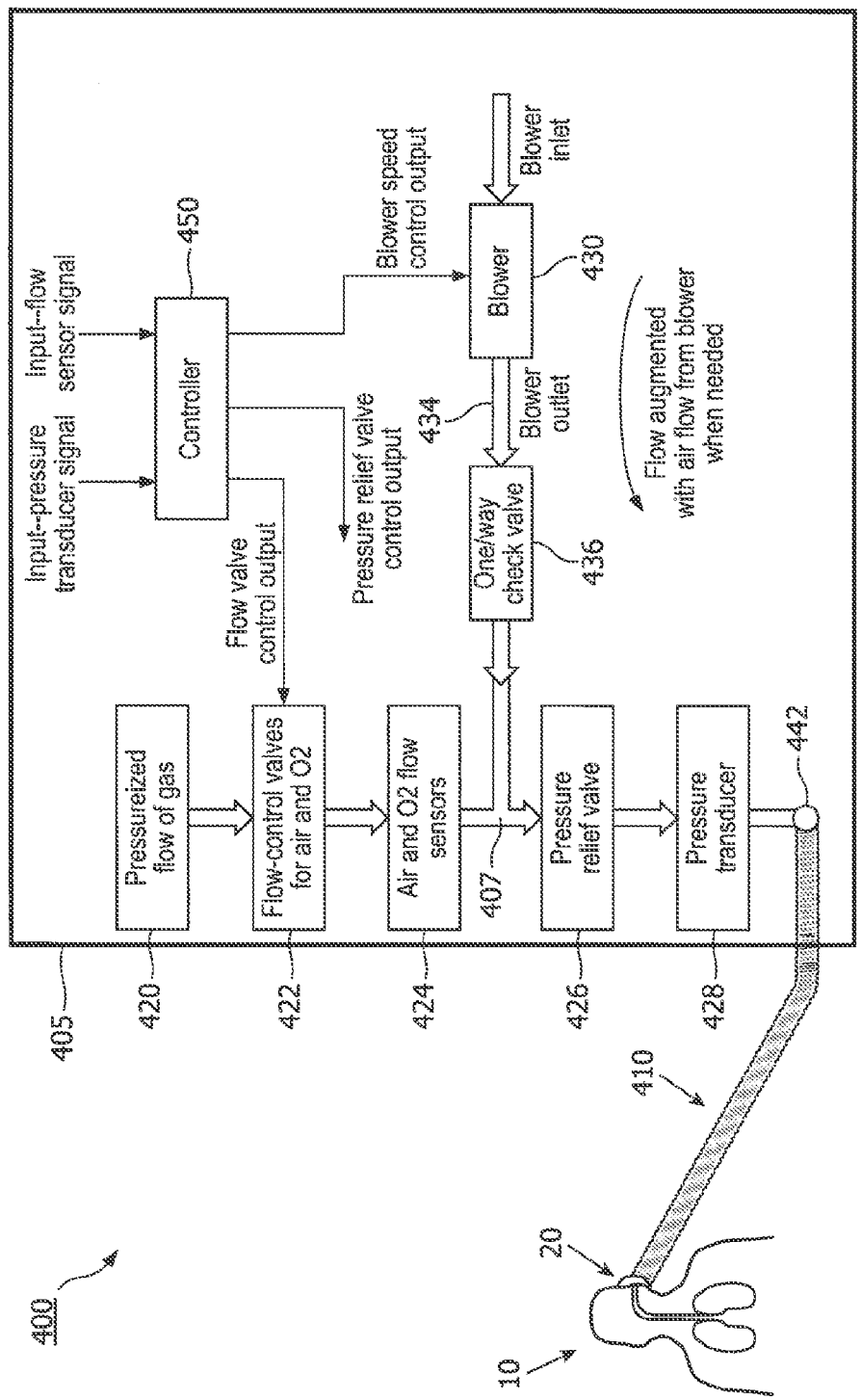
FIG. 4 is a detailed illustration of a third example embodiment of a ventilator system for noninvasive ventilation that includes a blower.

FIG. 4 is a detailed illustration of a third example embodiment of a ventilator system where an integrated blower may be used to generate positive pressure/flow to augment gas flow for noninvasive ventilation (NIV) where there may be limited flow of gas from a wall-outlet or compressor, or limited gas flow through flow valves and/or regulators of the gas supply device of the ventilator system.

Ventilator system 400 comprises a ventilator 405 with an integrated blower 430, and a single-limb patient circuit 410.

Ventilator 405 includes: a gas delivery device including a pressurized flow of gas 420 and one or more flow control valves 422 for oxygen and air; one or more air and oxygen flow sensors 424; a pressure relief valve 426; a pressure transducer 428; a blower 430 and an associated one-way check valve 436; and a controller 450. Ventilator 405 includes a patient circuit interface port 442 for connection to patient circuit 410. Ventilator 405 also includes a junction 407 for combining a pressurized flow of gas (e.g., oxygen and/or air) from the gas delivery device, and a pressurized flow of air from blower 430 to generate positive pressure.

Patient circuit 410 connects to a mask 20 for providing a pressurized flow of gas to patient 10. Mask 20 may include a passive exhalation port or an active exhalation port.

In some embodiments, the pressurized flow of gas 420 is received from an external supply (e.g., a tank), for example through a wall outlet.

In operation, controller 450 controls the gas delivery device (e.g., flow control valve(s) 422), blower 430, and pressure relief valve 426 in response to a patient airway pressure signal from pressure transducer 428 indicating the measured patient airway pressure, and a flow sensor signal from the one or more air and/or oxygen flow sensors 424 indicating the measured gas flow from the gas delivery device. Blower 430 supplements the flow supplied via the pressurized flow of gas 420, which is some cases may be limited, for example when ventilator 405 is connected to gas supply via a wall outlet. In that case, in some cases the gas flow from the pressurized flow of gas 420 may be limited to about 180 liters/minute. In some embodiments, by means of the supplemental flow of blower 430 via blower outlet 434, ventilator 405 is capable of providing a gas flow rate on the order of 250 to 300 liters/minute.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the scope of the appended claims.

What is claimed is:

1. A ventilator system (400) for supplementing a pressurized flow of gas from an external source to a patient, comprising:
    a patient circuit interface port (42) configured to be connected to a single-limb patient circuit (410);
    a gas delivery device including a pressurized flow of gas (420) operatively connected to the patient circuit interface port and configured to supply the pressurized flow of gas to the patient circuit interface port to generate positive pressure;
    a blower (430) having an outlet (434) operatively connected to the patient circuit interface port and configured to supply a pressurized flow of air to the patient circuit interface port in addition to and as a supplement to the pressured flow of gas from primary gas delivery device;
    a pressure transducer (428) configured to measure a gas pressure in the patient circuit;
    at least one flow sensor (424) configured to measure a gas flow in the patient circuit; and
    a controller (450) configured to control the gas delivery device and the blower in response to a pressure transducer signal indicating the measured pressure in the patient circuit and a flow sensor signal indicating the measured gas flow from the gas delivery device,
    wherein the gas delivery device and the blower together provide a gas flow rate in the range of about 250 to 300 liters per minute.

2. The ventilator system (400) of claim 1, wherein the gas delivery device includes flow control valves (422) for controlling a flow of the gas.

3. The ventilator system (400) of claim 2, wherein the controller controls the at least one flow control valve in response to the measured gas flow from the gas delivery device.

4. The ventilator system (400) of claim 1, further comprising a junction (407) for combining the pressurized flow of gas from the gas delivery device and the pressurized flow of air from the blower.

5. The ventilator system (400) of claim 4, further comprising a check valve (436) provided between the outlet of the blower and the junction.

6. The ventilator system (400) of claim 4, further comprising a pressure relief valve (426) between the patient circuit and the junction in communication with and controlled by the controller.

7. The ventilator system (400) of claim 1, further comprising a face mask (20) with one of a passive exhalation port or an active exhalation port.

* * * * *